June 18, 1946. A. F. ETTER Plant Pat. 699
APPLE TREE
Filed June 23, 1944
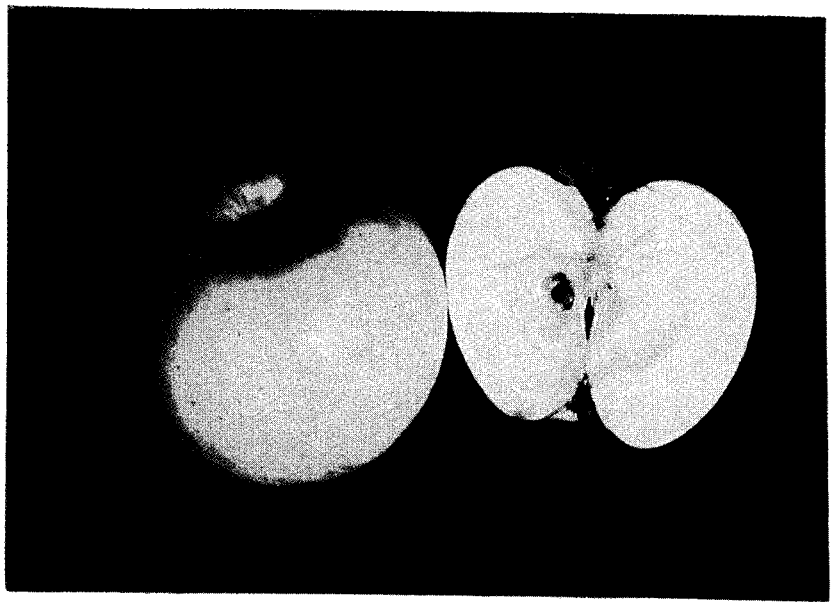
INVENTOR.
ALBERT F. ETTER.
BY
Chas. E. Townsend
ATTORNEY.

Patented June 18, 1946

Plant Pat. 699

UNITED STATES PATENT OFFICE

699

APPLE TREE

Albert F. Etter, Ettersburg, Calif., assignor to George C. Roeding, Jr., Niles, Calif.

Application June 23, 1944, Serial No. 541,687

1 Claim. (Cl. 47—62)

This invention relates to a new variety of apple tree characterized by the crispy coolness of its ripened fruit in October.

The fruit of this new variety is most nearly like the Bedfordshire Foundling. The skin of the new variety appears more polished than the Bedfordshire Foundling and whiter during similar stages of maturity. When the fruit of the new variety becomes fully mature, the skin assumes a yellowish hue, like the Bedfordshire Foundling. The flesh of the fruit of the new variety is distinctly white in appearance at all stages of growth, as distinguished from the ivory color of the fruit of the Bedfordshire Foundling variety.

The accompanying colored photograph illustrates this new discovery.

The following is a detail description of this new variety:

Size: The fruit is comparable to the Rhode Island Greening.
Stem: Short.
Calyx: Closed.
Basin: Open.
Skin: Polished; medium heavy.

Calyx tube: Narrow.
Core: Medium.
Seeds: Dark brown, medium size.
Flesh: White, tender, juicy.
Foliage: Large, heavy, and healthy.
Origin: The apple tree originated as a seedling of Bedfordshire Founding. The apple tree so resembles the Bedfordshire Foundling in external appearance as to bark, branches, and the like, as to make them incapable of positive identification by external examination of the trees when they are grown under like conditions.

The apple tree is especially characterized by very heavy fruit production. The tree is a regular bearer. The fruit of the tree is characteristically large.

What I claim is:

A new variety of apple tree substantially as herein disclosed, characterized by fruit having good size; skin polished, white during early stages of maturity and assuming a yellow hue at maturity; medium heavy skin, and white tender juicy flesh.

ALBERT F. ETTER.